US012725179B1

(12) United States Patent
Weinblatt

(10) Patent No.: US 12,725,179 B1
(45) Date of Patent: Sep. 1, 2026

(54) METHOD FOR MEASURING CONSUMER SACCADIC INTEREST BEFORE AND DURING MOMENT OF INTENT TO PURCHASE

(71) Applicant: Lee S. Weinblatt, Teaneck, NJ (US)

(72) Inventor: Lee S. Weinblatt, Teaneck, NJ (US)

( * ) Notice: Subject to any disclaimer, the term of this patent is extended or adjusted under 35 U.S.C. 154(b) by 0 days.

(21) Appl. No.: 18/629,631

(22) Filed: Apr. 8, 2024

Related U.S. Application Data

(63) Continuation-in-part of application No. 16/794,559, filed on Feb. 19, 2020, now abandoned.

(51) Int. Cl.
*G06Q 30/0242* (2023.01)
*A61B 5/16* (2006.01)

(52) U.S. Cl.
CPC ......... *G06Q 30/0242* (2013.01); *A61B 5/163* (2017.08); *A61B 2503/12* (2013.01)

(58) Field of Classification Search
None
See application file for complete search history.

(56) References Cited

U.S. PATENT DOCUMENTS

2015/0213634 A1* 7/2015 Karmarkar ............ G06T 11/001 345/589

FOREIGN PATENT DOCUMENTS

WO WO-2022263255 A1 * 12/2022 ......... G02B 27/0093

OTHER PUBLICATIONS

Dario D. Salvucci and Joseph H. Goldberg. 2000. Identifying fixations and saccades in eye-tracking protocols. In Proceedings of the 2000 symposium on Eye tracking research & applications (ETRA '00). Association for Computing Machinery, New York, NY, USA, 71-78. https://doi.org/10.1145/355017.355028 (Year: 2000).*

* cited by examiner

*Primary Examiner* — Katherine Kolosowski-Gager
(74) *Attorney, Agent, or Firm* — Natter & Associates, P.C.; Howard Natter

(57) ABSTRACT

A method for measuring consumer cognitive interest in stimuli before and during intent to purchase by utilizing saccadic eye vibration frequency detected by light beams reflected from the consumer eye. The viewed stimuli are simultaneously recorded and tagged in correspondence with vibration frequencies. Snippets of the recorded video containing the tags and video immediately preceding the tag are categorized for analysis of the effectiveness of the stimuli.

8 Claims, 2 Drawing Sheets

24
TAGGED RECORDED VIDEOS

26
RECOGNIZING TAGS AND SEPARATING VIDEOS TO FORM SNIPPETS

28
COMPILING SNIPPETS BY CATEGORIES

30
STORING SNIPPETS

METHOD FOR MEASURING CONSUMER SACCADIC INTEREST BEFORE AND DURING MOMENT OF INTENT TO PURCHASE

RELATED APPLICATIONS

The present application is a continuation in part of co-pending application Ser. No. 16/794,559 filed Feb. 19, 2020, which claims benefit of provisional application Ser. No. 62/025,196 filed Jul. 16, 2014, the entire disclosures of which are expressly incorporated by reference herein.

BACKGROUND OF THE INVENTION

Field of the Invention

This invention relates generally to consumer research methods and especially to a method for measuring emotive responses to stimuli to gain insight into the factors that contributed to a consumer's decision to make a purchase. In particular, the method of this invention is used to identify the stimuli that arouse a consumer's interest during the time leading up to and at the moment of intent to purchase.

Description of the Related Art

The commercial success of a consumer product is dependent, at least in part, upon stimuli that arouse an interest from a consumer. Advertisers not only want to measure consumer reactions while in a store and/or watching advertising media, they also want to discover the particular stimuli that provoke a positive interest, such as to find out more about the product, as well as the stimuli viewed at the moment of intent to purchase.

Although consumers may be interviewed when they leave a store or view a television program to evaluate consumer reaction to product packaging or other stimuli that convinced the consumer to make the purchase, this type of feedback has significant shortcomings. When questioned as to why they decided on one product over another product, often the consumer cannot remember the reason for the purchase decision, especially if it occurs at a subconscious level rather than through a deliberate and conscious process. Consumers may also be hesitant to say that a selection process was due to pricing, a nearby ad, or a display. Additionally, it may be difficult for a consumer to describe an emotive response after the fact, as the reason for the purchase decision. It should therefore be apparent that the data obtained from these previously used research techniques can be misleading, inaccurate, or otherwise unreliable.

Another research method is to provide consumers with a camera, or other imaging device, such as a smartphone, and to request the consumer to photograph the product of choice, the price, or other items of interest. The limitations of this method are that it is very time consuming, that the consumer may be embarrassed to record what is of interest, or that the consumer may forget to take the photograph; and furthermore, that this procedure does not provide information as to what led up to the purchase or item of interest decision.

Yet another method for determining a consumer's interest in visual stimuli, such as advertising or product packaging, is the use of eye-tracking data collected from the consumer. The eye-tracking data is used to identify the visual stimuli in the consumer's field of view as, for example, is disclosed in US Patent Application Publication No. 2013/0054576 to Karmarkar et al.

However, a problem with the use of eye-tracking, eye fixations, or eye gazing, is that although it may identify the stimuli in the viewer's field of view, it does not provide any insights into the viewer's cognitive processing of the scene viewed. For example, the viewer may have his/her thoughts on extraneous matters rather than on the stimuli being shown.

Another shortcoming of the above-mentioned method of tracking eye movement fixations is that it necessitates precise site alignment of camera and lighting for each viewer in accordance with the shape of the specific viewer's cornea to know exactly where the viewer is fixating.

In contrast, Applicant's method does not record fixations, and is concerned only with the speed of saccadic vibrations. This method can be used for in-store surveys with hidden cameras for capturing a viewer's saccadic eye vibrations since there is no need for viewer sight alignment. Further, because of the constant need to align the viewer's pupils to the eye-movement reflecting lights, Karmarkar's method sensitizes the respondent to the fact that he/she is being recorded rather than just putting on a pair of glasses and being asked to shop as with the Applicant's method.

SUMMARY OF THE INVENTION

Briefly, this invention concerns a consumer research method that utilizes saccadic eye vibrations for measuring the level of consumer interest in selected stimuli before and during the moment of intent to purchase.

An aspect of the method includes monitoring the frequency of the saccadic eye vibrations while viewing stimuli whereby the frequency is variable and increases as the consumer desires more visual information that is related to the cognitive level of consumer interest in the stimuli.

Another feature of the method includes selectively segmenting the recorded stimuli into snippets with each snippet reflecting the relative degree of consumer interest.

An additional benefit of the method is that it not only provides a record of the viewed stimuli at the moment of interest and/or intent to purchase but also provides a record of the stimuli preceding the moment of interest or intent to purchase.

It should therefore be apparent that the method does not rely upon consumer memory and/or time-consuming photographs for determining the effectiveness of advertising media such as described above.

Another advantage of the method is that it is more efficient, reliable, and accurate than the methods previously described.

BRIEF DESCRIPTION OF THE DRAWINGS

The invention will be described in more detail with reference to the drawings, wherein.

DETAILED DESCRIPTION OF THE INVENTION

With specific reference now to the figures in detail, it is stressed that the particulars shown are by way of example and for illustrative discussion of the preferred embodiment of the present invention and are presented in a cause of providing what is believed to be the most useful and readily understood description of the principles and conceptual aspects of the invention. In this regard, no attempt has been made to show aspects of the invention in more detail than is necessary for a fundamental understanding of the invention. The description, when taken together with the drawings, should make it apparent to those skilled in the art how the preferred form of the invention may be embodied in practice.

Figure 1:
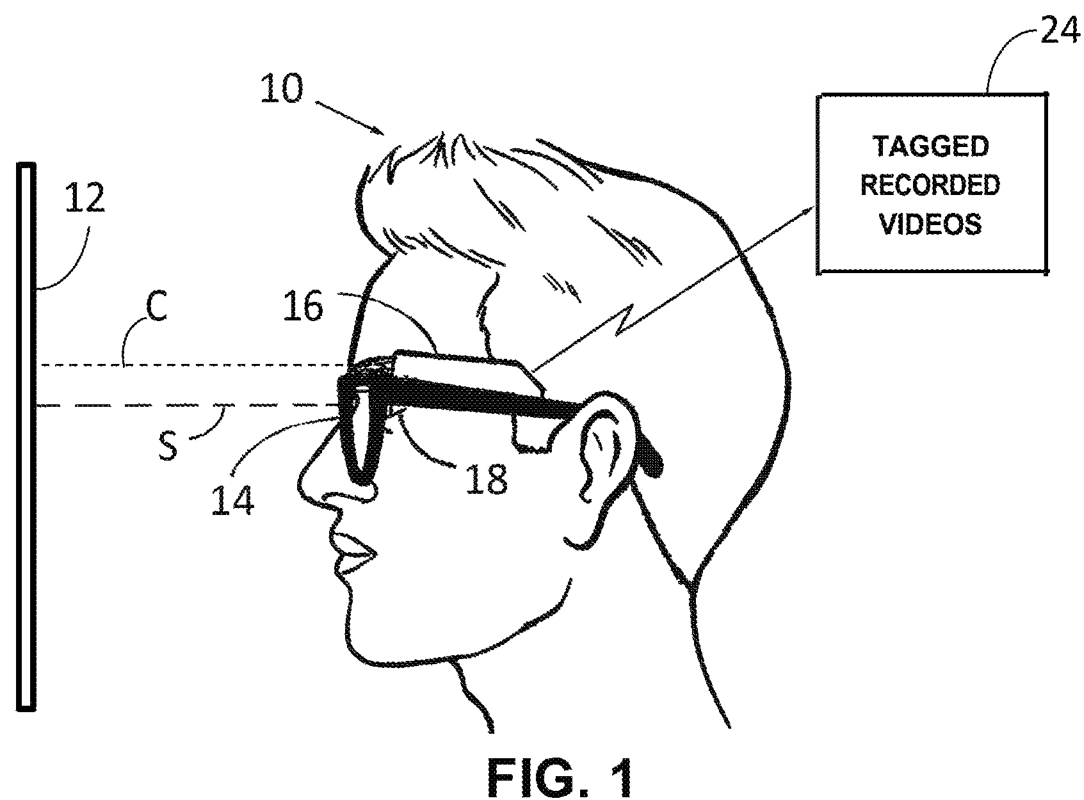
FIG. 1 is an illustration of a typical consumer being exposed to stimuli while wearing eyeglasses containing a recording camera.

Referring now in detail to FIG. 1 of the drawings, there is shown a typical consumer 10, exposed to stimuli 12, in a real or simulated environment, such as product packaging, retail shelf displays, television viewings, advertising media, and the like; the consumer line of sight is indicated as "S". The consumer 10 is provided with eyeglasses 14, having an integral recording camera 16, or equivalent recording headgear. The camera 16 is intended to simultaneously record the stimuli 12 being viewed by the consumer 10; the camera sight line is indicated as "C"; the recorded stimuli 12 is further subject to index tagging as will be described herein.

Figure 2:
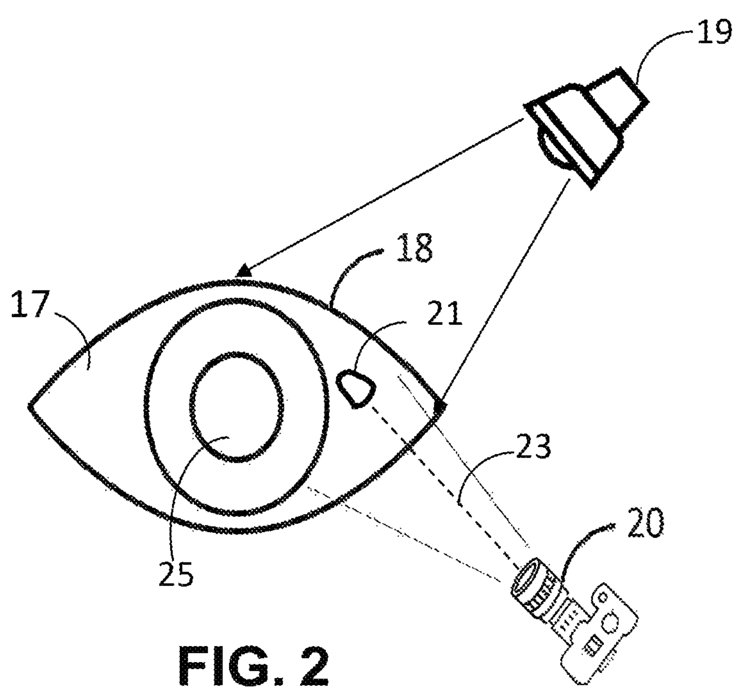
FIG. 2 is a depiction of the tracking of saccadic eye movement with a motion-sensing recording camera.

The reaction of the consumer 10 to the stimuli 12 is preferably monitored using a high-speed motion-sensing camera 20 to detect saccadic eye movement. In this exemplary embodiment, motion sensing of the saccadic eye movement of the consumer 10 is shown in FIG. 2, wherein there is depicted an isolated view of a consumer eye 18 and the high-speed motion-sensing camera 20. The camera 20, is positioned in proximity to eye 18 of the consumer 10 and functions in combination with a light radiation source 19, which is directed at the consumer eye 18. The light radiation is reflected from the consumer eye as beams of light that move concurrently with the eye movement. The movement of the light beams is captured by camera 20. In this preferred embodiment, eye 18 is illuminated by infrared light radiation that is nearly invisible to humans. The infrared light directed at the cornea 17 is reflected by a cornea surface aberration or imperfection 21.

The imperfection can include visible markings such as spider veins, dips in the cornea surface, abrasions, or lesions. The imperfection 21 provides a reference marker for tracking the corresponding eye movement for detection and recordation of the frequency variation of eye movement over time. Alternatively, the infrared radiation can also illuminate the retina 25 which can be seen with a magnifying lens attached to the camera 20. During saccadic eye movement, the retina will move with the eye to shift the fovea (the area of the retina with the highest density of receptors) from one point to another. This eye movement will be detected by camera 20, and then electronically processed and wirelessly transmitted to a receptor in the recording camera 16 for generating an index tag associated with the location of the frequency relative to the corresponding stimuli. It has also been found that alternative forms of radiation, such as low-intensity light radiation, can be used with low-light sensitive cameras in place of infrared radiation.

Figures 2A, 3:
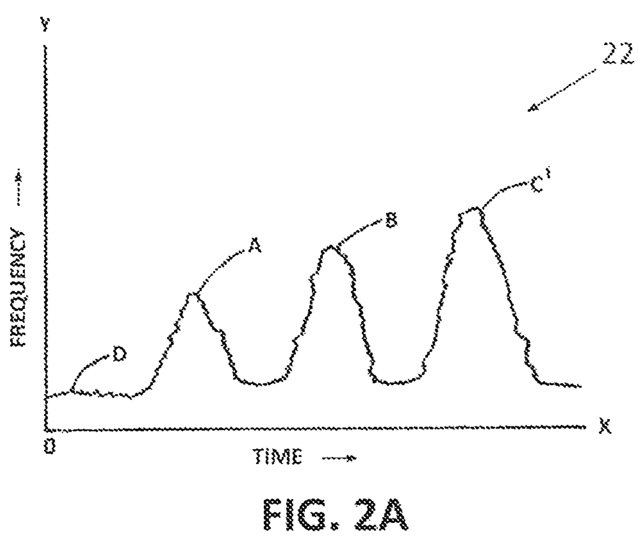
FIG. 2A is a graphic representation of a typical time vs frequency graph of eye movement.
FIG. 3 is a flow chart illustrating the processing of the tagged video frames transmitted from the eyeglasses recording camera.

With reference to FIG. 2A, there are graphically represented at 22 variations in the frequency of eye movement shown along the Y axis as a function of time shown along the X axis. When the consumer 10 is simply gazing at the stimuli 12 without any particular interest the eye movement is relatively low as denoted at D.

The eye movement at various points of interest are shown progressively at the peaks A, B, and C' with C' being the point of greatest interest. These parameters denoted respectively at A, B, and C' can be tagged on the recorded video for identifying corresponding portions of the recorded stimuli that were of interest as well as the degree of interest expressed by the frequency of the eye movement. For example, the letter A can be considered to denote a slight degree of interest, the letter B can represent moderate interest and the letter C' signifies an intense interest as during an intent to purchase. The areas on the graph designated D refer to stimuli of little or no interest. Index tabs are accordingly added to the recorded video corresponding to locations A, B, and C'. Turning next to the processing of the recorded video, with reference to the flow-chart in FIG. 3, the recorded video having the index tags 24 is initially processed by a computer 26 having software for reading to recorded video and creating snippets from the recorded video.

The snippets are segments of the recorded video that contain the index tags and include a portion of the recorded video just prior to the tag, typically approximately 1 to 5 seconds before the tag. The snippets are then compiled by a computer 26 having software for combining the snippets by categories defined by the intensity of interest as, for example, reflected by the index tabs corresponding to locations A, B, and C'. The categorization can result in categories of recorded video in which the consumer had slight interest, moderate interest, or intense interest, for example, when consumer interest was piqued or when consumer interest was intense as when ready to make a purchase. This arrangement will facilitate analysis of the effectiveness of the stimuli 12. The combined snippets are then optionally stored in the "cloud" 30 or equivalent computer storage, for later retrieval and examination.

In view of the foregoing, it should now be apparent that there is provided a method for measuring consumer interest before and during a moment of intent to purchase that is well adapted to meet conditions of practical use. Since other modifications might be made in the exemplary embodiment set forth and method described herein, it is to be understood that the above is to be interpreted in an illustrative sense and not in a limiting sense.

Having thus described the invention there is claimed as new and desired to be secured by Letter Patent:

1. A consumer research method exclusively utilizing saccadic eye vibrations for measuring the level of consumer cognitive interest in selected stimuli before and during moment of intent to purchase comprising the steps of:

a) exposing the consumer to selected visual stimuli of images presented in at least one of an on-screen and live format;

b) recording the images of the stimuli being viewed by the consumer using an optical imaging device;

c) projecting light radiation on at least one eye of the consumer for illuminating at least one of the retina and the cornea;

d) recording the frequency variations of consumer saccadic eye vibrations while viewing the images, with a motion-sensing camera for monitoring the corresponding movement of the light radiation reflected from the eye of the consumer regardless of eye tracking motion, eye fixation and eye gaze direction, wherein the vibration frequency varies directly with the cognitive level of consumer interest in the viewed stimuli;

e) transmitting the frequency variations of the saccadic eye vibrations from the motion-sensing camera to a receptor in the optical imaging device, said optical imaging device generating an index tag for identifying respective images of the recorded stimuli with the corresponding saccadic eye vibration frequency whereby the level of consumer interest in each of the respective images of the recorded stimuli can be analyzed by frequency variation for determining the cognitive interest level of the consumer in the stimuli;

f) slicing the images to form snippets defined by the index tags, and g) combining the snippets, by frequency variations, into categories of at least one of slight, moderate, and intense frequency variation reflecting the relative degree of consumer interest.

2. A consumer research method utilizing saccadic eye vibrations for measuring the level of consumer interest in selected stimuli before and during moment of intent to purchase as claimed in claim 1 wherein the snippet defined by the index tag includes at least one of the identified images appearing before and after the index tag for analysis of the effectiveness of the stimuli.

3. A consumer research method utilizing saccadic eye vibration frequency, for measuring the level of consumer interest as claimed in claim 1 wherein the projected light radiation is infrared radiation.

4. A consumer research method utilizing saccadic eye vibration frequency for measuring the level of consumer interest as claimed in claim 1 wherein the projected light radiation is directed to the cornea of the consumer eye.

5. A consumer research method utilizing saccadic eye vibration frequency for measuring the level of consumer interest as claimed in claim 4 wherein the projected light radiation is reflected from an aberration in the surface of the cornea.

6. A consumer research method utilizing saccadic eye vibration frequency for measuring the level of consumer interest as claimed in claim 1 wherein the light radiation reflected from the cornea of the eye is detected with a motion-sensing recording camera.

7. A consumer research method utilizing saccadic eye vibration frequency for measuring the level of consumer interest as claimed in claim 6 wherein the motion-sensing camera detects eye vibrations that correspond to the movement of light that is reflected from the cornea.

8. A consumer research method utilizing saccadic eye vibrations for measuring the level of consumer interest in selected stimuli before and during moment of intent to purchase as claimed in claim 1 wherein the light radiation is reflected from an aberration in at least one of the cornea and the retina.

* * * * *